United States Patent
Boggess et al.

(10) Patent No.: US 11,808,750 B2
(45) Date of Patent: Nov. 7, 2023

(54) SOLID-PHASE SAMPLING DEVICE AND METHODS FOR POINT-SOURCE SAMPLING OF POLAR ORGANIC ANALYTES

(71) Applicant: SAVANNAH RIVER NUCLEAR SOLUTIONS, LLC, Aiken, SC (US)

(72) Inventors: Andrew J. Boggess, Aiken, SC (US); Stephen L. Crump, Martinez, GA (US); Thomas L. White, Evans, GA (US)

(73) Assignee: Battelle Savannah River Alliance, LLC, Aiken, SC (US)

( * ) Notice: Subject to any disclaimer, the term of this patent is extended or adjusted under 35 U.S.C. 154(b) by 273 days.

(21) Appl. No.: 17/244,167

(22) Filed: Apr. 29, 2021

(65) Prior Publication Data
US 2021/0263002 A1  Aug. 26, 2021

Related U.S. Application Data

(62) Division of application No. 16/170,185, filed on Oct. 25, 2018, now Pat. No. 11,022,593.

(51) Int. Cl.
*G01N 33/18* (2006.01)
*G01N 1/10* (2006.01)
*G01N 1/40* (2006.01)

(52) U.S. Cl.
CPC ........... *G01N 33/1826* (2013.01); *G01N 1/10* (2013.01); *G01N 1/405* (2013.01)

(58) Field of Classification Search
CPC ....... G01N 33/1826; G01N 1/10; G01N 1/405
(Continued)

(56) References Cited

U.S. PATENT DOCUMENTS

| 4,975,378 A | 12/1990 | Banerjee |
| 6,541,273 B1 | 4/2003 | Plaisance |

(Continued)

FOREIGN PATENT DOCUMENTS

| CN | 107102071 | 8/2017 | |
| WO | WO 2004/106914 | * 12/2004 | ............. G01N 30/00 |

(Continued)

OTHER PUBLICATIONS

Annesley, et al. "Glucuronidation of prodrug reactive site: isolation and characterization of oxymethylglucuronide metabolite of fosphenytoin" *Clin. Chem.* 47 (2001) pp. 910-918.

(Continued)

*Primary Examiner* — Christine T Mui
(74) *Attorney, Agent, or Firm* — Dority & Manning, P.A.

(57) ABSTRACT

Sampling devices for sampling an aqueous source (e.g., field testing of ground water) for multiple different analytes are described. Devices include a solid phase extraction component for retention of a wide variety of targeted analytes. Devices include analyte derivatization capability for improved extraction of targeted analytes. Thus, a single device can be utilized to examine a sample source for a wide variety of analytes. Devices also include an isotope dilution capability that can prevent error introduction to the sample analysis and can correct for sample loss and degradation from the point of sampling until analysis as well as correction for incomplete or poor derivatization reactions. The devices can be field-deployable and rechargeable.

14 Claims, 5 Drawing Sheets

(58) Field of Classification Search
USPC .......................................................... 436/178
See application file for complete search history.

(56) References Cited

U.S. PATENT DOCUMENTS

| | | |
|---|---|---|
| 6,790,673 B1 | 9/2004 | Kingston |
| 7,531,134 B1 | 5/2009 | Anderson et al. |
| 7,666,686 B2 | 2/2010 | Shelly, Jr. et al. |
| 8,383,420 B2 | 2/2013 | Kingston et al. |
| 2002/0155034 A1 | 10/2002 | Perman et al. |
| 2002/0155614 A1 | 10/2002 | Tomlinson et al. |
| 2005/0079544 A1 | 4/2005 | Nguyen et al. |
| 2005/0276727 A1 | 12/2005 | Pawliszyn et al. |
| 2006/0118491 A1 | 6/2006 | Gjerde et al. |
| 2007/0117222 A1 | 5/2007 | Sibanda et al. |
| 2010/0178710 A1 | 7/2010 | Hamon et al. |
| 2011/0306147 A1 | 12/2011 | Laurent et al. |
| 2012/0181232 A1 | 7/2012 | Chen |
| 2014/0158881 A1 | 6/2014 | Cooper |
| 2016/0071713 A1 | 3/2016 | Farmer, III et al. |

FOREIGN PATENT DOCUMENTS

| | | |
|---|---|---|
| WO | WO 2008/112032 | 9/2008 |
| WO | WO 2017/214549 | 12/2017 |

OTHER PUBLICATIONS

Boggess, A. "Novel Solid-Phase Extraction Techniques for Biological and Environmental Analysis Using Isotope Dilution Mass Spectrometry" *Duquesne U.* (2015) pp. 1-208.

Köke, et al. "Multi-layer solid-phase extraction and evaporation—enrichment methods for polar organic chemicals from aqueous matrices" *Anal. Bioanal. Chem.* 410 (2018) pp. 2403-2411.

Monperrus, et al. "Simultaneous Sample Preparation and Species-Specific Isotope Dilution Mass Spectrometry Analysis of Monomethylmercury and Tributyltin in a Certified Oyster Tissue" *Anal. Chem.* 75 (2003) pp. 4095-4102.

Smith, et al. "Quantification of monohydroxy-PAH metabolites in urine by solid-phase extraction with isotope dilution-GC-MS" *Anal. Bioanal. Chem.* 372 (2002) pp. 216-220.

Wagner, et al. "Sensitive and stable pre-calibrated solid-phase extraction cols. for environmental and forensic quantification using isotope dilution mass spectrometry" *Anal. Meth.* 7 (2015) pp. 4285-4294.

* cited by examiner

SOLID-PHASE SAMPLING DEVICE AND METHODS FOR POINT-SOURCE SAMPLING OF POLAR ORGANIC ANALYTES

CROSS REFERENCE TO RELATED APPLICATION

This application is a Divisional Application of U.S. patent application Ser. No. 16/170,185, having a filing date Oct. 25, 2018, entitled "Solid-Phase Sampling Device and Methods for Point-Source Sampling of Polar Organic Analytes," which is incorporated herein by reference in its entirety.

FEDERAL RESEARCH STATEMENT

This invention was made with Government support under Grant No. DE-AC09-085R22470, awarded by the U.S. Department of Energy. The Government has certain rights in the invention.

BACKGROUND

Accurate detection of the presence or quantity of organic contaminants in aqueous samples, e.g., ground water samples, presents many difficulties as a single sample source can carry multiple different contaminants with a wide variety of chemistries. Moreover, many organic contaminants are volatile or quick to degrade, and as such, their presence in a sample may be underestimated or missed altogether due to loss or degradation in the time period from the initial sampling to the testing protocol. This may be particularly problematic for samples obtained from natural sources, as transportation and storage time between sampling and testing can be extensive. Polar organic contaminants present additional difficulties, as their hydrophilicity make analysis from an aqueous sample quite difficult.

Attempts have been made to improve aqueous sample testing. For instance, solid phase extraction (SPE) is often used with aqueous samples for pre-concentration procedures to capture and determine the presence/quantity of organic contaminants. Unfortunately, SPE presents difficulties when targeting polar organic analytes and is particularly problematic when a sample includes multiple different (e.g., both polar and nonpolar) organic analytes. Moreover, SPE requires the use of calibration curves in quantification techniques and includes the potential of error introduction at many processing points.

A technique that has been developed in an attempt to improve quantitative accuracy of sample analysis is isotope dilution analysis. Isotope dilution analysis involves addition of isotopically labeled analogues (also termed a spike) into a sample. Using known data including isotopic abundances, concentration and mass of the isotopically labeled spike, mass of the targeted analyte, and sample quantity, the concentration of an analyte can be calculated mathematically without the use of calibration curves. Isotope dilution analysis can correct for many analysis errors introduced due to, e.g., sample preparation, poor reproducibility, sample loss, low analyte recovery, instrumental drift, matrix effects, and physical or chemical interferences. Unfortunately, the spike is combined with the sample immediately prior to analysis, and as such, this method may not account for analyte loss/degradation that occurs following collection of a sample and prior to analysis and, as such, is not suitable for many applications including field use.

What are needed in the art are methods and materials that can accurately assess the concentration of potential contaminants, and in particular polar organic contaminants, in an aqueous sample.

SUMMARY

According to one embodiment, disclosed is sampling device that can beneficially be compact and portable for use in sampling an aqueous source for one or multiple targeted analytes. A sampling device can include a liquid inlet, a first layer downstream of the inlet, a second layer downstream of the first layer, and a liquid outlet downstream of the second layer. The first layer can include a SPE medium and can also include a derivatizing agent for a targeted analyte (e.g., a polar analyte). Reaction between the targeted analyte and the derivatizing agent can form a derivatized analyte. The second layer can also include a SPE medium, which can be the same or can differ from the SPE medium of the first layer. The second layer also includes an isotopically labeled analogue of the derivatized analyte.

Also disclosed are methods for using a sampling device. For instance, a method can include introducing an aqueous sample into a sampling device. As the sample contacts the first layer, targeted polar analytes in the sample can contact the derivatizing agent and react with the agent to form a derivatized analyte. The derivatized analyte, being less polar than the targeted polar analyte, can interact with the SPE media of the device and be retained on the media at a detectable level. The isotopically labeled analogue of the derivatized analyte can also interact with the SPE media, and the two (the derivatized analyte and the isotopically labeled analogue) can come to equilibrium with the derivatizing agent and with the SPE media. After the non-retained portion of the aqueous sample exits the device through the outlet, the device can be transported and/or stored for a period of time prior to analysis. The method can also include eluting retained materials from the SPE media following the storage/transport period and analyzing the eluent to determine the concentration of the targeted polar analyte in the aqueous sample.

Methods for forming the devices are also disclosed. For instance, a method can include loading a device housing with the first and second layers such that the first layer is downstream of the liquid inlet and the second layer is downstream of the first layer. The first and second layers can include first and second SPE media, respectively. A method can also include loading the first layer with the derivatizing agent and loading the second layer with the isotopically labeled analogue of the derivatized analyte. In general, the layers can be loaded with the derivatizing agent and the isotopically labeled analogue prior to loading the layers into the device housing. In one embodiment, the devices can be reusable, and a method can include removing the SPE media following elution of a sample and reloading the housing with fresh media for re-use.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
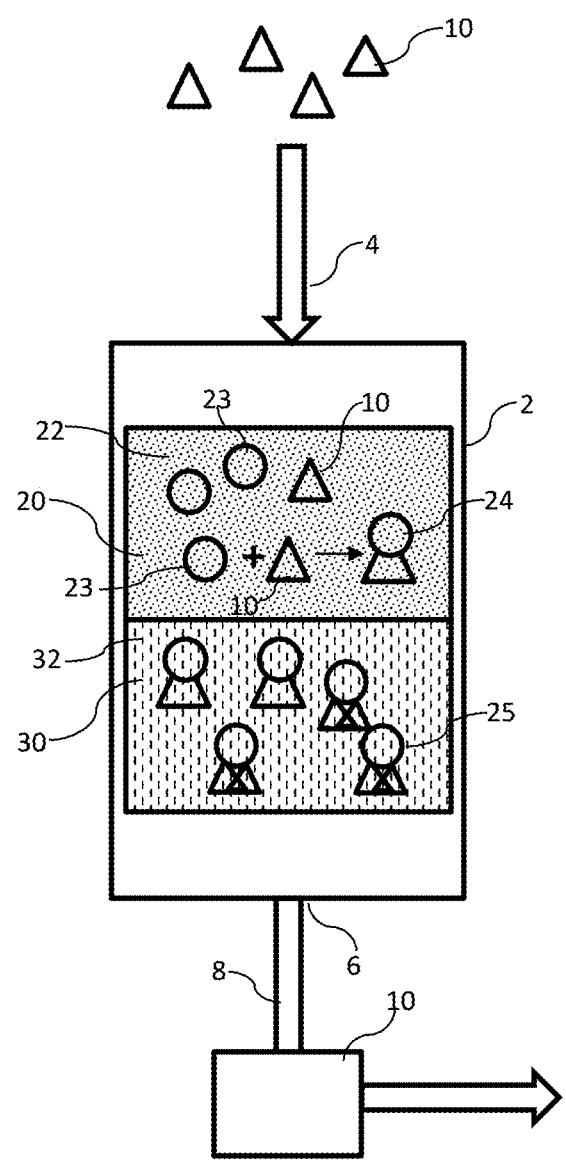
FIG. 1 schematically illustrates one embodiment of a sampling device.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment may be used in another embodiment to yield a still further embodiment.

In general, disclosed are sampling devices that can be beneficially utilized in one embodiment for sampling an aqueous source (e.g., field testing of ground water) for multiple different analytes. The device can be small and portable, as well as disposable or re-chargeable, and can store a sample for a period of time (e.g., during transport from a source and prior to analysis) and still provide accurate analysis of the analyte concentration in the sample.

More specifically, disclosed devices provide for targeted analyte derivatization and solid-phase extraction in conjunction with isotope dilution in a single, portable device. The SPE component of the devices provides for retention of a wide variety of targeted analytes. The analyte derivatization capability allows for extraction of polar compounds simultaneously with nonpolar compounds, and by such, a single device can be utilized to examine a sample source for a wide variety of analytes. The isotope dilution aspect of the devices can prevent error introduction to the sample analysis and can correct for sample loss and degradation from the point of sampling until analysis, allowing for samples to be stored for long periods of time. Moreover, the isotope dilution aspect can correct for incomplete or poor derivatization reactions. Thus, the devices can be field-deployable and can provide accurate analysis of any water source, no matter how remote, for a wide variety of analytes, and in particular, for potential contaminants.

Polar organic analytes are notoriously difficult to accurately assess in aqueous samples, and disclosed devices can solve many problems associated with these materials. FIG. 1 schematically illustrates one embodiment of a device for use in sampling a polar organic analyte 10 as may be found in an aqueous sample. A device can include a housing 2, as well as an inlet 4 and an outlet 6. While there is no particular limitation on the size of a device, in one embodiment, the housing 2 can be relatively small so as to be compact and portable for sampling in the field. For instance, the housing 2 can be cubic, cylindrical, or any other convenient shape, and in one embodiment, can have a width and depth of from about 1 inch to about 6 inches and a height of from about 3 inches to about 10 inches. The material of formation of the housing is not particularly limited, though in one embodiment, the housing can be formed of a plastic material that can provide resiliency and light weight to the device.

The inlet 4 and outlet 6 can include closures and one or both of the inlet 4 and the outlet 6 can be permanently or removably attachable tubing, which can allow for control of the liquid flow into and/or out of the housing. For instance, the outlet 6 can connect to plastic tubing 8 that can in turn be connectable to a vacuum pump 10 that can be used in those embodiments in which organic materials retained within the housing 2 are dried following collection from an aqueous sample and prior to transport, storage, and/or analysis.

A first layer 20 and a second layer 30 are located within the housing 2. As shown, the layers 20, 30 are located within the housing 2 such that a sample introduced to the device via inlet 4 will contact the first layer 20 prior to contacting the second layer 30.

The first layer 20 includes a first SPE media 22 and the second layer 30 includes a second SPE media 32. Depending upon the nature of the SPE media, the layers 20, 30 can also include suitable retention devices for the SPE media. For instance, in those embodiments in which the SPE media are in the form of porous particulates, the layers can include retention devices, such as wire or plastic mesh or the like, that can retain the SPE media in the desired location within the housing. Adhesives or the like that do not prevent desired association between a sample and the SPE media can also be used to retain the SPE media in a defined layer within the housing, for instance in the form of a removable cartridge that can be located and retained at a predetermined location within the housing.

The SPE media 22, 32 can be the same or can differ from one another and can vary depending upon the nature of the analytes targeted for retention by use of the device. For instance, in those embodiments in which an aqueous sample is to be analyzed for polar and/or nonpolar organic analytes, the SPE media 22, 32 can include any solid phase extraction sorbent that can be utilized for a range of polar and nonpolar compounds. Examples of suitable solid phase extraction sorbents include, without limitation, carbon-based media such as porous particular carbon molecular sieves (e.g., Carbosieve® absorbents), graphitized polymer carbon (e.g., spherical graphitized polymer carbon), graphitized carbon black (GCB), pyrocarbon reinforced GCB; silica-based media; etc.

In addition to the SPE media 22, the first layer 20 also includes a derivatizing agent 23. The derivatizing agent 23 can be selected for reaction with a targeted analyte 10 such that upon interaction, reaction between the derivatizing agent 23 and the targeted analyte 10 can form a derivatized analyte 24, as indicated in FIG. 1.

Analytes as may be collected and analyzed by use of disclosed devices are not particularly limited and can generally include any analyte of interest as may be found in an aqueous sample. In general, the targeted analytes will encompass relatively low molecular weight organic analytes, e.g., having a number average molecular weight of about 500 g/mol or less, about 250 g/mol or less, or about 100 g/mol or less in some embodiments. In one embodiment, targeted analytes can encompass potential contaminants of ground water. Exemplary targeted analytes can include, without limitation, perchloroethylene, tetrachloroethylene, benzene, toluene, xylene, ethylbenzene, polychlorinated biphenyl isomeric congeners, and halogenated pesticides and herbicides including alachlor, atrazine, bromacil, cyanazine, endrin, heptachlor, metolachlor, and chlorpyrifos.

Basic derivatizing reactions can include, for example, silylation, acylation, and alkylation, with the preferred derivatizing reaction depending upon the polarity of the targeted analyte and that of the reaction product as well as the chemical nature of the SPE media. In general, it can be desired that the reaction product be less polar than the analyte, and as such will exhibit a better solid-liquid distribution coefficient with the SPE medium, i.e., the derivatized analyte will be retained by the SPE media with higher preference as compared to the non-derivatized targeted analyte.

Derivatizing agents can also be selected through determination of the ease/speed of derivatization of the targeted analyte by the derivatizing agent. For instance, when considering a silylation derivatization, alcohols are much more efficiently silylized as compared to amide, and as such, if the targeted analyte is an alcohol, it may be preferred to select a silylating derivatizing agent. However, when selecting a derivatizing agent for an amide-containing targeted analyte, it may be preferred to select a different derivatizing agent that is more efficient for the amide-containing targeted analyte, e.g., an acylating derivatizing agent.

Silylating derivatizing agents can be selected for derivatization of targeted analytes including, without limitation, alcohols, amines, amides, aldehydes, thiols, phenols, enols, and carboxylic acids. Examples of silylating derivatizing agents can include, without limitation, alkylsilanes or arylsilane such as derivatives of trimethylsilyl-, t-butyl dimethyl silyl or other alkylsilyl- or arylsilyl agents. Specific examples of silylating derivatizing agents can include, without limitation, N-methyl-N-(trimethylsilyl)trifluoroacetamide, N-tert-butyldimethylsilyl-N-methyltrifluoroacetamide, 1,3-bis(chloromethyl)-1,1,3,3-tetramethyldisilazane, 1-(trimethylsilyl)imidazole, 3-trimethylsilyl-2-oxazolidinone, allyl(chloro)dimethylsilane, bromotrimethylsilane, chlorotriethylsilane, chlorotriisopropylsilane, chlorotrimethylsilane, hexaethyldisiloxane, hexamethyldisilazane, N,N'-bis(trimethylsilyl)urea, N,N-dimethyltrimethylsilylamine, N,O-bis(trimethylsilyl)acetamide, N-methyl-N-trimethylsilylacetamide, N-methyl-N-trimethylsilylheptafluorobutyramide, trimethylsilyl methanesulfonate, trimethylsilyl N,N-dimethylcarbamate, trimethylsilyl trifluoromethanesulfonate, triphenylsilane, methyl 3-trimethylsiloxy-2-butenoate, phenylchlorosilane, or triethylsilane or mixtures thereof.

Acylation can be selected for derivatization of targeted analytes including, but not limited to, amines, amides, alcohols, thiols, phenols, enols, glycols, unsaturated compounds, and aromatic rings. Examples of acylating derivatizing agents can include, without limitation, acid anhydrides, acid halides, reactive acyl derivatives such as acrylated imidazoles, acrylated amides, alkali metal salts of carboxylic acids, and acrylated phenols. Specific examples of acylating derivatizing agents can include, without limitation, acyl chlorides or other acyl halides, acetic anhydride, propionic acid anhydride, mixed anhydrides of acetic and propionic acids, acetyl chloride, butyric acid chloride, benzoyl chloride, propionic acid chloride, stearyl chloride, alkali metal salts of carboxylic acids having between two and eight carbon acids, nitrophenyl carbonate, trichlorophenyl carbonate, pentachlorophenyl carbonate, and carbonyl imidazole, as well as various active esters, e.g. nitrophenyl ester, pentafluoroethyl ester, trichlorophenyl ester.

Alkylating derivatizing agents can be selected for derivatization of targeted analytes including, without limitation, carboxylic acids, amines, amides, alcohols, thiols, phenols, and enols. Examples of alkylating derivatizing agents can include, without limitation, alkyl halides, dialkyl sulfates, nitro-substituted chloro- or fluoro-benzenes, and alkylammonium salts. Specific examples of alkylating derivatizing agents include, without limitation, benzyl chloride, methyl chloride, alpha-chloroacetic acid, dimethyl sulfate, alpha-chloromethyl phosphoric acid, tetraalkylammonium hydroxides, dimethylformamide dialkyl acetals, and diazoalkanes.

Referring again to FIG. 1, upon the derivatization reaction in the first layer 20 of the device, the liquid sample will flow to contact the second layer 30 of the device. The second layer 30 contains an isotopically labeled analogue 25 of the derivatized analyte 24. In one embodiment, the isotopically labeled analogue can be a carbon-13 labeled analogue, but the devices and methods are not limited to carbon-13 labeled analogues, and any stable analogue of the derivatized analyte can be utilized, including but not limited to deuterium labeled analogues. The derivatized analytes, the isotopically labeled analogues, and the derivatizing agents of the device can come into equilibrium with one another within the device. The isotope of the isotopically labeled analogue will generally not be in a position on the analogue where it can interact or react with the derivatizing agent, as it (the isotope) could then be lost via a reverse reaction during equilibration.

Upon interaction of the liquid sample with both of the first layer 20 and the second layer 30, the two layers can act upon one another synergistically to induce in-phase equilibration of the derivatized analyte 24 and the isotopically labeled analogue 25. As is known, derivatization can be imprecise and incomplete and materials retained on SPE media can degrade over time. As such, following the initial derivatization interaction and equilibrium between the various components and the SPE media, a portion of the targeted analyte in the sample, as well as a portion of the isotopically labeled analogue, can be lost as the sample flows through the device during sample collection as well as during transport/storage of the device prior to elution of the retained materials from the SPE media and analysis of the eluent. However, as the loading level of the isotopically labeled analogue is known, and as the isotopically labeled analogue and the derivatized analyte will be subject to the same conditions from the time of sampling until the time of analysis, determination of the loss (if any) of the isotopically labeled analogue in this period can be used to mathematically correct the analysis results regarding the concentration of targeted analyte in the original sample due to e.g., incomplete derivatization, sample loss, degradation, volatility, interferents, etc.

Figure 2:
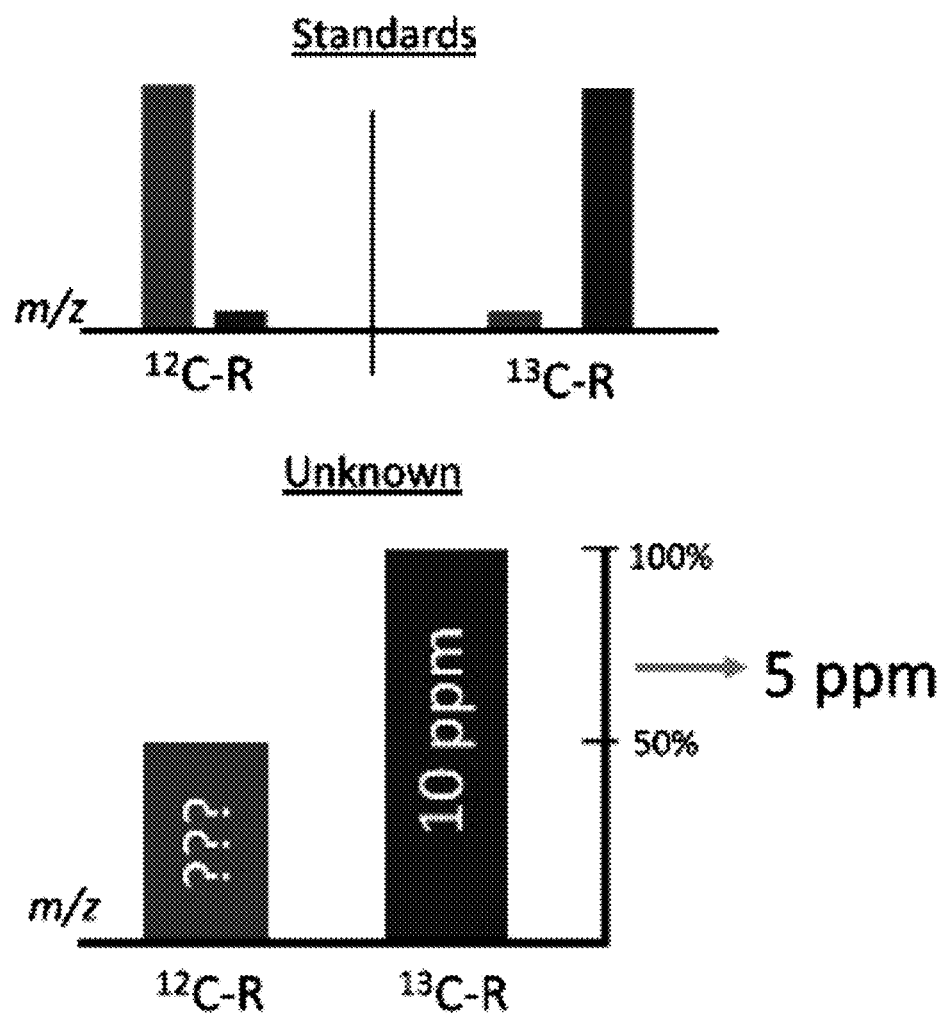
FIG. 2 illustrates one embodiment of an isotope dilution analysis profile.

For instance, and with reference to FIG. 2, m/z standards for a natural compound ($^{12}$C-R) and an isotopically labeled analogue ($^{13}$C-R) are shown, which demonstrate the relative amounts of the carbon-12 compound and the carbon-13 compound for each material. The lower graph of FIG. 2 illustrates an exemplary m/z result as may be obtained upon mass chromatography analysis of a sample following elution from a device that includes both the natural compound and the isotopically labeled spike. As the initial quantity of the isotopically labeled analogue loaded into the device is known, degradation/loss of the isotopically labeled analogue in the eluent can be determined from the analysis results for the isotopically labeled analogue. This information can then be utilized to apply a correction factor to the analysis results for the derivatized analyte, so as to obtain an accurate concentration of the targeted analyte in the initial sample.

Figure 3:
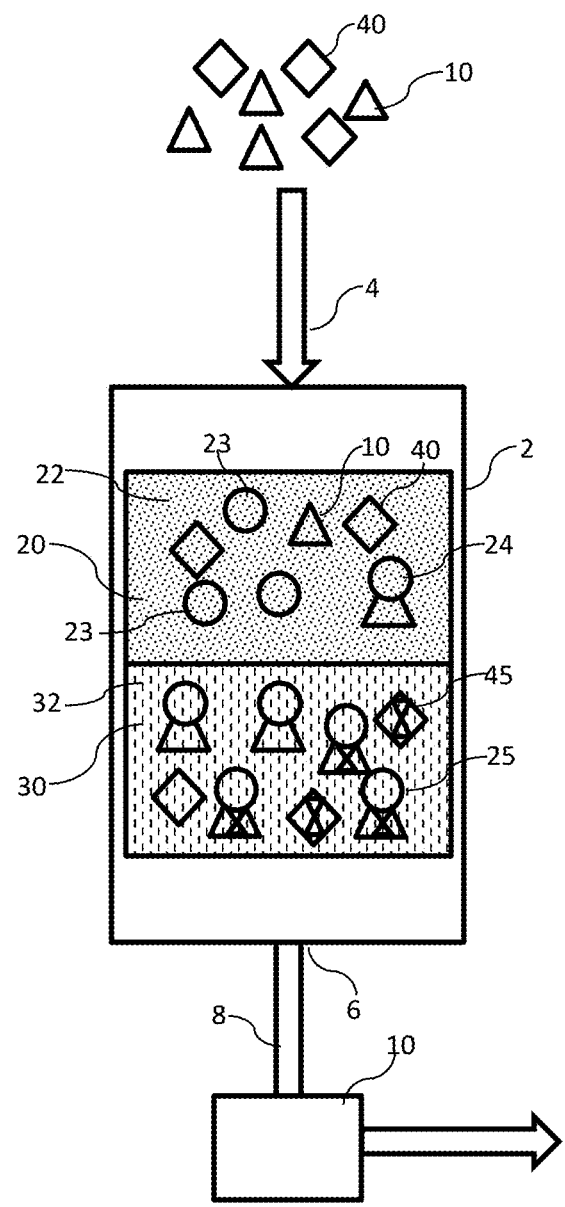
FIG. 3 schematically illustrates another embodiment of a sampling device.

Devices can be utilized to determine the concentration of several different analytes in a sample, even when those analytes exhibit different chemistries. For instance, FIG. 3 illustrates one embodiment of a device that can be utilized in determining the concentration of a first targeted polar organic analyte 10 as well as a nonpolar organic analyte 40.

As the nonpolar organic analyte 40 can already exhibit good retention characteristics on the SPE media 22, 32, the device need not include a derivatization agent for the nonpolar organic analyte. However, to improve quantitative detection of the nonpolar organic analyte in a sample, the device can include an isotopically labeled analogue 45 of the nonpolar organic analyte 40. This isotopically labeled analogue 45 can be loaded into a device in a known quantity and as such, can be utilized to determine a correction factor for any loss or degradation of the nonpolar organic analyte 40 from the time of collection until the time of elution and analysis.

Figure 4:
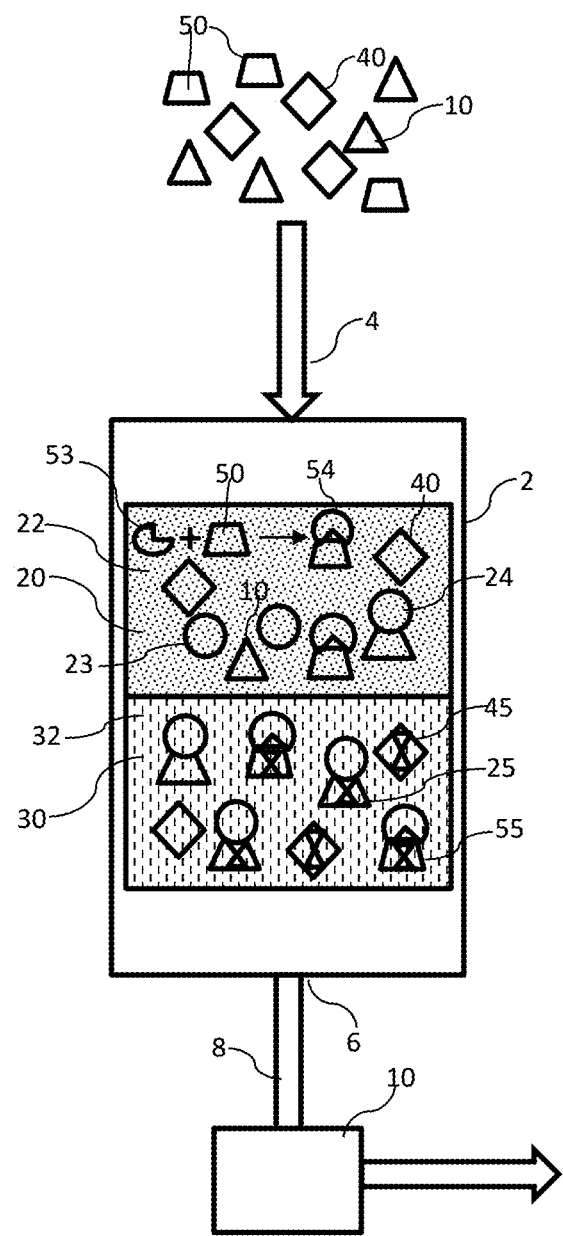
FIG. 4 schematically illustrates another embodiment of a sampling device.

In another embodiment, a device can be designed to capture and analyze the concentration of one or more additional polar and/or nonpolar organic analytes in a sample. For instance, as illustrated in FIG. 4, a device can be designed to capture both a first targeted analyte 10 and a second targeted analyte 50, both of which being polar organic analytes. The device can be designed to also capture a nonpolar organic analyte 40 (or multiple nonpolar organic analytes, as desired). As such, in addition to the components of the device discussed previously (derivatizing agent 23 for the first targeted analyte 10, isotopically labeled analogue 25 of the derivatized analyte 24, isotopically labeled analogue 45 of the nonpolar organic analyte 40), the device can include a second derivatizing agent 53 loaded in the first layer 20. The second derivatizing agent 53 can be selected for derivatization of the second targeted analyte 50. As shown, reaction of the second targeted analyte 50 with the second derivatizing agent 53 can form a second derivatized analyte 54. The second derivatizing agent 53 can be the same or can differ from the derivatizing agent 23 used for the first targeted analyte 10, generally depending upon the nature of the targeted analytes.

The device of FIG. 4 can also include an isotopically labeled analogue 55 that is an analogue of the second derivatized analyte 54. As described previously, the presence of a known quantity of the isotopically labeled analogue 55 loaded into the second layer 30 of the device can be used to mathematically correct the analysis results regarding the concentration of the second targeted analyte 50 in the sample. Thus, upon analysis of the retained materials on the device, an accurate concentration of all of the targeted analytes can be obtained.

Figure 5:
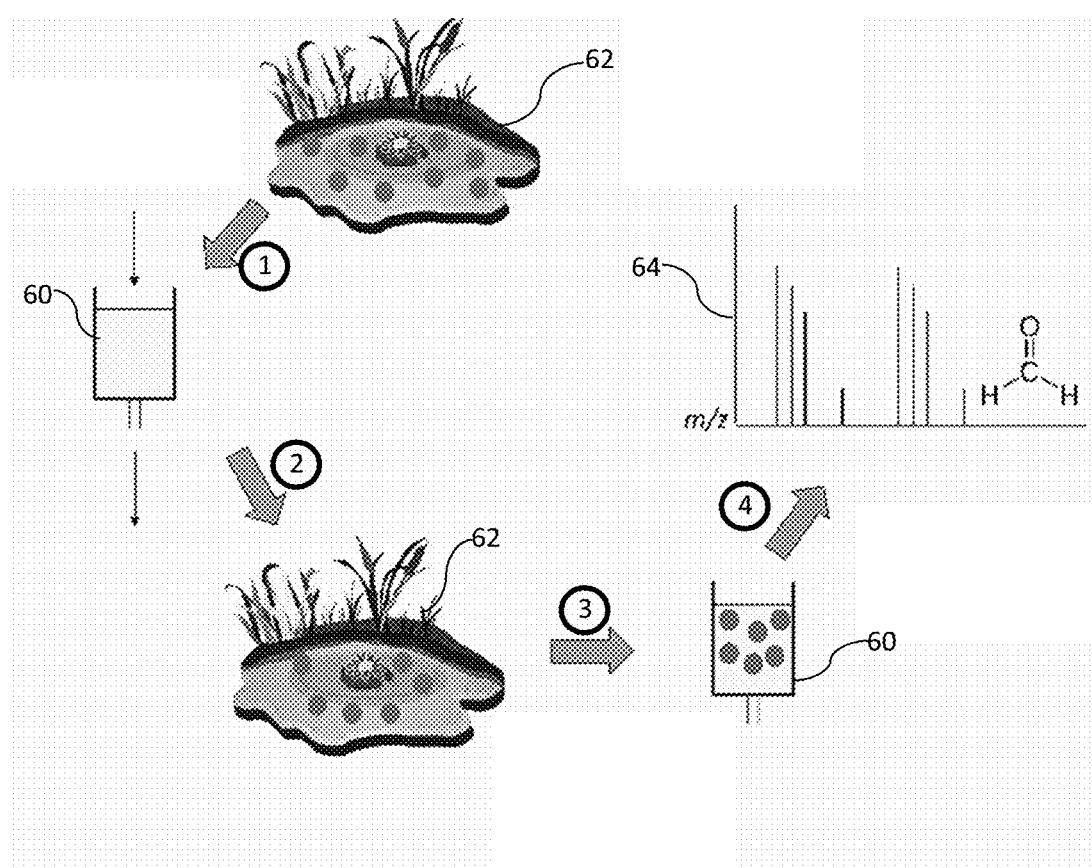
FIG. 5 schematically illustrates one method for utilizing a sampling device.

FIG. 5 schematically illustrates one embodiment of a method for using the sampling devices. As shown, a device 60 can be utilized for field sampling, e.g., at a surface pond 62, as shown. The device 60 can be pre-loaded with the first and second layers and the various derivatizing agents and isotopically labeled analogues, as discussed above. Possible storage time for a device prior to loading with the layers and active agents and prior to use can generally depend on the exact analytes and derivatizing agents used, but in general, a device can provide increased accuracy if utilized within a few weeks (e.g., about a month) of formation.

An aqueous sample is collected and passed through the device at step 1, during which the various components can come to equilibrium with one another and the sample components that are not retained in the device are returned to the sample source at step 2. Thus, the bulk of the liquid of the sample is left at the source while the targeted analytes are retained in the device. Optionally, the retained components can be dried (e.g., by use of a vacuum pump) and the dried, loaded device can be transported and optionally stored (step 3) prior to elution and analysis via, e.g., mass spectrometry (step 4). Elution can be carried out with typical solvents, with the preferred solvent for any protocol generally depending upon the particular analytes and derivatizing agents involve. By way of example, solvents can include, without limitation, hexane, methylene chloride, chloroform, diethyl ether, ethyl acetate, acetone, acetonitrile, isopropanol, methanol, and acetic acid. Following, the eluent can be analyzed via mass spectrometry to identify the isotopes of the various components.

In one embodiment, the device can be rechargeable, in which case the used media (e.g., self-supporting media cartridges) can be removed from the housing and the housing can be re-loaded with fresh media that has been charged with derivatizing agents and isotopically labeled analogues for re-use.

Beneficially, the device can be small (e.g., easily carried by hand), lightweight, cost-effective, disposable or re-usable, and provide highly accurate data with regard to analyte concentration in an aqueous sample source. In one embodiment, the device can be effectively used by researchers or industry involved in sampling in locations where the transport of large amounts of sample source would be cumbersome and inefficient as well as in more accessible locations for relatively simple, inexpensive, and accurate water sampling (e.g., household use). For instance, following collection of a sample, a device can be sealed and transported via shipping to a testing location, with the testing results then returned to the sender. By way of example, a device can be used for EPA certification of a water source under several EPA approved testing methods (e.g., Methods 6800, 1624, 1625).

While certain embodiments of the disclosed subject matter have been described using specific terms, such description is for illustrative purposes only, and it is to be understood that changes and variations may be made without departing from the spirit or scope of the subject matter.

What is claimed is:

1. A sampling device comprising:
    a liquid inlet;
    a first layer downstream of the liquid inlet, the first layer comprising a first solid phase extraction medium, the first layer further comprising a first derivatizing agent for a first targeted analyte, reaction between the first derivatizing agent and the first targeted analyte forming a first derivatized analyte;
    a second layer downstream of the first layer, the second layer comprising a second solid phase extraction medium, the second layer further comprising an isotopically labeled analogue of the first derivatized analyte; and
    a liquid outlet downstream of the second layer.

2. The sampling device of claim 1, wherein the first solid phase extraction medium and/or the second solid phase extraction medium comprises a carbon-based medium, the first solid phase extraction medium and the second solid phase extraction medium being the same or differing from one another.

3. The sampling device of claim 1, wherein the first derivatizing agent comprises a silylation derivatizing agent, an acylation derivatizing agent, or an alkylation derivatizing agent.

4. The sampling device of claim 1, wherein the isotopically labeled analogue of the first derivatized analyte is a carbon-13 labeled analogue.

5. The sampling device of claim 1, wherein the first layer and the second layer are components of first and second self-supporting removable cartridges, respectively.

6. The sampling device of claim 1, further comprising a housing that contains the first layer and the second layer, the housing having a width of from about 1 inch to about 6 inches, a depth of from about 1 inch to about 6 inches, and a height defined between the liquid inlet and the liquid outlet of from about 3 inches to about 10 inches.

7. The sampling device of claim 1, the first layer further comprising a second derivatizing agent for a second targeted analyte, reaction between the second derivatizing agent and the second targeted analyte forming a second derivatized analyte, the second layer further comprising an isotopically labeled analogue for the second derivatized analyte.

8. The sampling device of claim 1, further comprising an isotopically labeled analogue for a third targeted analyte in the second layer.

9. A method for forming the sampling device of claim 1 comprising:
  locating the first layer in a housing downstream of the liquid inlet, the liquid inlet being defined in a portion of the housing; and
  locating the second layer in the housing downstream of the first layer; wherein the housing defines the liquid outlet downstream of the second layer.

10. The method of claim 9, wherein the first layer and the second layer are removably held within the housing.

11. The method of claim 9, further comprising loading the first derivatizing agent onto the first layer prior to locating the first layer in the housing.

12. The method of claim 9, further comprising loading the isotopically labeled analogue of the first derivatized analyte onto the second layer prior to locating the second layer in the housing.

13. The method of claim 9, the first layer further comprising a second derivatizing agent, reaction between the second derivatizing agent and a second targeted analyte forming a second derivatized analyte, the second layer further comprising an isotopically labeled analogue of the second derivatized analyte.

14. The method of claim 13, the second layer further comprising an isotopically labeled analogue of a third targeted analyte.

* * * * *